(12) United States Patent
Huang et al.

(10) Patent No.: US 12,234,442 B2
(45) Date of Patent: Feb. 25, 2025

(54) INTELLIGENT BACTERIAL COLLECTION SYSTEM

(71) Applicant: HANGZHOU DIANZI UNIVERSITY, Zhejiang (CN)

(72) Inventors: Xuefeng Huang, Zhejiang (CN); Shengji Li, Zhejiang (CN); Youping Gong, Zhejang (CN); Jiangrong Xu, Zhejiang (CN)

(73) Assignee: HANGZHOU DIANZI UNIVERSITY, Zhejiang (CN)

( * ) Notice: Subject to any disclaimer, the term of this patent is extended or adjusted under 35 U.S.C. 154(b) by 861 days.

(21) Appl. No.: 17/406,089

(22) Filed: Aug. 19, 2021

(65) Prior Publication Data

US 2021/0380924 A1 Dec. 9, 2021

(30) Foreign Application Priority Data

Jun. 29, 2021 (CN) .......................... 202110725507.3

(51) Int. Cl.
*C12M 1/00* (2006.01)
*C12M 1/12* (2006.01)
*C12M 1/26* (2006.01)
*C12M 3/00* (2006.01)

(52) U.S. Cl.
CPC ............ *C12M 33/00* (2013.01); *C12M 23/04* (2013.01); *C12M 23/44* (2013.01); *C12M 23/48* (2013.01); *C12M 23/50* (2013.01); *C12M 29/00* (2013.01)

(58) Field of Classification Search
CPC ...... C12M 23/04; C12M 23/08; C12M 23/44; C12M 23/48; C12M 23/50; C12M 29/00; C12M 33/00; C12M 41/48
See application file for complete search history.

(56) References Cited

U.S. PATENT DOCUMENTS

2021/0324318 A1* 10/2021 Parietti .................. C12M 23/42

FOREIGN PATENT DOCUMENTS

| CN | 110511872 A | * | 11/2019 | ............. B65G 57/04 |
| EP | 3068870 B1 | * | 1/2020 | ............. C12M 23/50 |
| WO | WO-2015101326 A1 | * | 7/2015 | ............. C12M 23/44 |

\* cited by examiner

*Primary Examiner* — Lydia Edwards

(57) ABSTRACT

An intelligent bacteria collection system includes a bottle opening module and a peristaltic pump module opposite to each other, wherein a guide rail is arranged between the bottle opening module and the peristaltic pump module, and a tray module is placed on the guide rail; a manipulator module and the peristaltic pump module are fixed on an infusion operation platform; a control infusion module is placed on the tray module, which can be moved to and fixed on the infusion operation platform by the manipulator module. The present invention replaces the conventional artificial bacteria collection process, makes the bacteria collection process more rapid, reduces the possible secondary pollution in the manual detection operation process, improves the accuracy of the bacteria collection detection, and improves the work efficiency. The present invention provides high degree of automation, wherein no manual operation is required in the bacteria collection process.

19 Claims, 11 Drawing Sheets

INTELLIGENT BACTERIAL COLLECTION SYSTEM

CROSS REFERENCE OF RELATED APPLICATION

The present invention claims priority under 35 U.S.C. 119(a-d) to CN 202110725507.3 filed Jun. 29, 2021.

BACKGROUND OF THE PRESENT INVENTION

Field of Invention

The present invention relates to a technical field of intelligent sterile inspection systems, and more particularly to an intelligent bacteria collection system for test samples with different test varieties and different packaging specifications.

Description of Related Arts

As the key to food and drug quality control, sterility inspection is an important item for enterprises and regulatory agencies to inspect qualified products, and requirements therefor are cleared listed in the latest 2011 edition of the "Good Manufacturing Practice for Pharmaceuticals (Revised in 2010)" (GMP), the 2015 edition of "Pharmacopoeia of the People's Republic of China" (referred to as the Chinese Pharmacopoeia), and the United States pharmacopeia USP31-NF26 "71" sterility test. The sterility test of the test samples can adopt the membrane filtration method and the direct inoculation method. Usually, the sterility test of the test sample will adopt the membrane filtration method. However, if there is no suitable membrane filtration technology, the medium direct inoculation method will be used. Membrane filtration generally uses a closed filter with microporous membrane, wherein the pore size of the membrane for sterility inspection should not be greater than 0.45 μm, and a recommended diameter is about 50 mm. When using the membrane filtration method, dilution and washing may be needed according to the situation, and finally a culture medium is used for culture and observation for 14 days to judge whether the test sample is contaminated. According to different test samples, dilution volume, washing times, and medium type will be different, so the sterility inspection device must adapt to the changes of the test samples. Typical test samples include: aqueous solution test sample, water-soluble solid test sample, non-water-soluble test sample, descent and viscous oil test sample soluble in isopropyl myristate, sterile gas (spray) test sample, syringe test sample filled with medicine, test sample of medical device with catheter (blood transfusion, infusion bag, etc.), etc. At the same time, the inspection quantity and inspection volume of the test samples are also clearly stipulated.

Conventionally, the bacteria collection operations involved in sterility inspection all rely on manual operations, which have low automation, integration and intelligence levels, leading to low efficiency of sterility inspection. The key processes such as bacteria collection and cleaning will be greatly affected by personnel. And there will be significant differences in sterility inspection results and efficiency due to the operations of different personnel. The conventional sterility testing process faces with the problems of multiple sample types, multiple sample packaging specifications, multi-process analysis, non-continuous operation, and low bacteria collection analysis efficiency. Therefore, it is necessary to invent an intelligent bacteria collection system and method to solve such problems.

SUMMARY OF THE PRESENT INVENTION

An object of the present invention is to provide an intelligent bacteria collection system.

Accordingly, the present invention comprises: a guide rail, a tray module, a manipulator module, a peristaltic pump module, a flipping mechanism module, and a control infusion module; wherein the tray module is placed on the guide rail; the peristaltic pump module is provided on one side of the tray module, and a tray positioning device is provided on the other side of the tray module; the manipulator module and the peristaltic pump module are fixed on an infusion operation platform; the infusion operation platform is equipped with a liquid outlet device; the control infusion module is placed on the tray module, which is transported to and fixed on the infusion operation platform by the manipulator module;

the tray module comprises: a tray, a moisturizing cleaning solution bottle, a culture medium bottle, a test sample, a container adaptor, and the control infusion module placed on the tray; wherein the tray is used to place items, and the moisturizing cleaning solution bottle is used to clean a culture bottle in the control infusion module; the container adaptor is used to place the culture medium bottle to facilitate grasping of a flipping mechanism; the control infusion module is used for infusion and bacteria collection of the culture bottle;

the control infusion module comprises a first hose mounting assembly, a first needle, a fixed support plate, a tube fixing seat, a horizontal clamp, a culture device tooling, a tube clamp, a movable blade knife and the culture bottle; wherein the fixed support plate fixes and supports all parts; the first hose mounting assembly comprises a hose clamp and one or more infusion tubes; the infusion tubes are fixed on the hose clamp, and one end of each of the infusion tubes is connected to the first needle through a pipeline, and the other end of each of the infusion tubes is connected to a culture bottle inlet through the horizontal clamp, the tube clamp, and the movable blade knife in turn; the culture bottle is placed in the culture device tooling; a cap stopper fixing assembly, the tube clamp and the movable blade knife are provided on a top of the culture device tooling; an under-bottle pipe blocking assembly is provided on the fixed support plate at a bottom of the culture device tooling; one side of the movable blade knife is connected to a tension spring; an infusion tube installation hole and an upper cap stopper are arranged on a top of the culture bottle; an under-bottle pipe is arranged at a bottom of the culture bottle; a filter is provided inside the culture bottle; liquid in the culture bottle is discharged to a liquid outlet device through the under-bottle pipe; the cap stopper fixing assembly is arranged opposite to the upper cap stopper to drive the upper cap stopper to move vertically relative to the culture device tooling; the under-bottle pipe is arranged opposite to a lower cap stopper in the under-bottle pipe blocking assembly to drive the lower cap stopper to move vertically;

the peristaltic pump module comprises a first peristaltic pump and a second peristaltic pump; each of the peristaltic pumps has a hose mounting assembly installation slot; the flipping mechanism module comprises a first flipping mechanism and a second flipping mechanism; the first flipping mechanism is provided on one side of the first peristaltic pump, and the second flipping mechanism is provided on one side of the second peristaltic pump; the first flipping mechanism and the first peristaltic pump are provided on one side of the manipulator module, and the second flipping mechanism and the second peristaltic pump are provided on the other side of the manipulator module;

a first imitation bottle head is provided on the container adaptor, a second imitation bottle head is provided on the first hose mounting assembly, a third imitation bottle head is provided on the first needle, a fourth imitation bottle head is provided on the tube fixing seat, a fifth imitation bottle head is provided on the cap stopper fixing assembly, and a sixth imitation bottle head is provided on the under-bottle pipe blocking assembly.

The intelligent bacteria collection system further comprises: a bottle opening module opposite to the peristaltic pump module; wherein the tray module further comprises a transition bottle, a multi-needle tooling, a discharging groove, a second needle, and a second hose mounting assembly; the second hose mounting assembly comprises a hose clamp and one or more infusion tubes; the infusion tubes are fixed on the hose clamp, and one end of each of the infusion tubes is connected to the second needle through a pipeline, and the other end of each of the infusion tubes is connected to a liquid outlet of the multi-needle tooling; a quantity of the infusion tubes is equal to a quantity of the liquid outlet of multi-needle tooling; a seventh imitation bottle head is provided on the multi-needle tooling; a needle mounting plate is provided in the bottle opening module; the discharging groove is used to contain bottle head wastes generated by the bottle opening module after bottle opening.

The transition bottle is filled with a dissolving liquid.

The bottle opening module comprises a linear module, a bottle opening lifting cylinder, a liquid pumping lifting cylinder, a bottle head nesting plate, a breaking plate, a top cover plate, a top cover cylinder, a bottle opening breaking cylinder, the needle mounting plate, and a pin cylinder; the bottle opening lifting cylinder and the liquid pumping lifting cylinder are connected to and driven by the linear module to move horizontally; the bottle opening lifting cylinder is connected to and drives the bottle head nesting plate to move vertically; the top cover plate is arranged above the bottle head nesting plate, and is connected to and driven by the top cover cylinder to move horizontally; the top cover plate and the top cover cylinder are both set on the bottle opening lifting cylinder to move with the bottle head nesting plate; the bottle head nesting plate is connected to and driven by the bottle opening breaking cylinder through the breaking plate, so as to move horizontally; the liquid pumping lifting cylinder is connected to and drives the needle mounting plate to move vertically; the pin cylinder and a clip slot are arranged on the needle mounting plate, which are matched with mounting holes of the multi-needle tooling to fix the multi-needle tooling; a bottle head nesting hole is drilled on the bottle head nesting plate, and a rubber band is placed in the bottle head nesting hole.

The bottle opening module comprises a body, a linear module, a bottle opening device, a discharging device, and a liquid pumping device; the linear module, the bottle opening device, the discharging device and the liquid pumping device are all arranged on the body; the linear module is arranged on a top of the body, and is connected to the bottle opening device, the discharging device and the liquid pumping device through a module adapter plate; the module adapter plate is connected to a connecting plate on the linear module; the bottle opening device and the discharging device are arranged on one side of the module adapter plate, and the liquid pumping device is arranged on the other side of the module adapter plate; the bottle opening device comprises a first push rod motor, an inclined breaking plate, and a spring push rod; the first push rod motor is fixed on the one side of the module adapter plate, and the inclined breaking plate is fixed on an output shaft of the first push rod motor, in such a manner that the first push rod motor drives the inclined breaking plate to move vertically; during bottle opening, a discharge side of the bottle opening device is arranged opposite to an inlet side of the discharging device; the pumping device comprises a second push rod motor, an intermediate connecting plate, a suction needle adapter, and the needle mounting plate; the second push rod motor is arranged on the other side of the module adapter plate; the intermediate connecting plate is fixed on an output shaft of the second push rod motor, and is connected to the suction needle adapter; the needle mounting plate is also connected to the suction needle adapter; the needle mounting plate is used to fix the multi-needle tooling.

Tray support rods are provided at four corners of the tray for stacking multiple trays.

Quantities of the horizontal clamp, the culture device tooling, the tube clamp, the movable blade knife, and the culture bottle are identical and corresponding to each other, and are equal to a quantity of the infusion tubes in the first hose mounting assembly.

The culture device tooling comprises a first culture device tooling, a second culture device tooling, a third culture device tooling, and a fourth culture device tooling; the cap stopper fixing assembly, the tube clamp and the movable blade knife are provided on a top of the culture device tooling; the first culture device tooling and the second culture device tooling are fixed on the fixed support plate, which fix left and right sides of the culture bottle and limit the cap stopper fixing assembly; the third culture device tooling is mounted on middle top portions of the first culture device tooling and the second culture device tooling, which fixes the top of the culture bottle, as well as limits and fixes the clamp tube and the movable blade knife; the fourth culture device tooling is mounted on middle portions of the first culture device tooling and the culture device tooling, which fixes a middle of the culture bottle; the under-bottle pipe blocking assembly is provided on the fixed support plate at the bottom of the culture device tooling.

The cap stopper fixing assembly comprises an upper cap stopper clamping plate and an upper cap stopper fixing plate; cooperating holes are arranged between the upper cap stopper clamping plate and the upper cap stopper fixing plate.

The under-bottle pipe blocking assembly adopts a lever structure.

The liquid outlet device comprises a liquid outlet diversion tank, a feeding cylinder, and a waste liquid recovery tank; a hole is drilling on a top of the liquid outlet diversion tank which has a hollow inside; a liquid outlet port is provided at a bottom of the liquid outlet diversion tank, and the waste liquid recovery tank is provided at the liquid outlet port; the feeding cylinder is connected to and drives the liquid outlet diversion tank to move forward and backward, so that the hole at the top of the liquid outlet diversion tank is connected to a liquid outlet port of the under-bottle pipe of the culture bottle.

The tray positioning device comprises a cylinder and a positioning pin; the cylinder drives the positioning pin to cooperate with a side hole of the tray, thereby positioning the tray.

The manipulator module comprises a mechanical arm and a mechanical gripper; the mechanical gripper comprises a bearing connector, a sliding cylinder, and a bottle head holding part; the bearing connector is connected to the mechanical arm; the sliding cylinder drives the bottle head holding part to loosen and fasten, so as to hold a bottle head or an imitation bottle head tightly.

Each flipping mechanism comprises a sliding table, a sliding table cylinder, and a flipping base; the sliding table is arranged on the flipping base, and is connected to the sliding table cylinder; the sliding table cylinder drives the sliding table to open and close.

The present invention replaces the conventional artificial bacteria collection process, makes the bacteria collection process more rapid, reduces the possible secondary pollution in the manual detection operation process, improves the accuracy of the bacteria collection detection, and improves the work efficiency. The present invention provides high degree of automation, wherein no manual operation is required in the bacteria collection process, and the operation of the bacteria collection device can be controlled by a programmable logic controller (PLC) to complete the entire bacteria collection process. The present invention shows a high degree of adaptability, and can perform bacteria collection detection for test solution bottles such as ampoules, vials, and large-volume bottles. The present invention provides high degree of reliability: the entire device is operated under aseptic conditions for avoiding indirect pollution from the outside world, thereby ensuring high detection accuracy.

DETAILED DESCRIPTION OF THE PREFERRED EMBODIMENT

The present invention will be further described with the accompanying drawings. The entire device is operated under aseptic conditions.

The present invention is implemented for 10 ml ampoule bottled aqueous solution test sample, 10 ml vial bottled water-soluble solid test sample, and 250 ml and 100 ml multi-layer large-volume bottled aqueous solution test sample. In embodiments, each cylinder is equipped with a magnetic switch sensor for movement state feedback of the cylinder.

Figure 1:
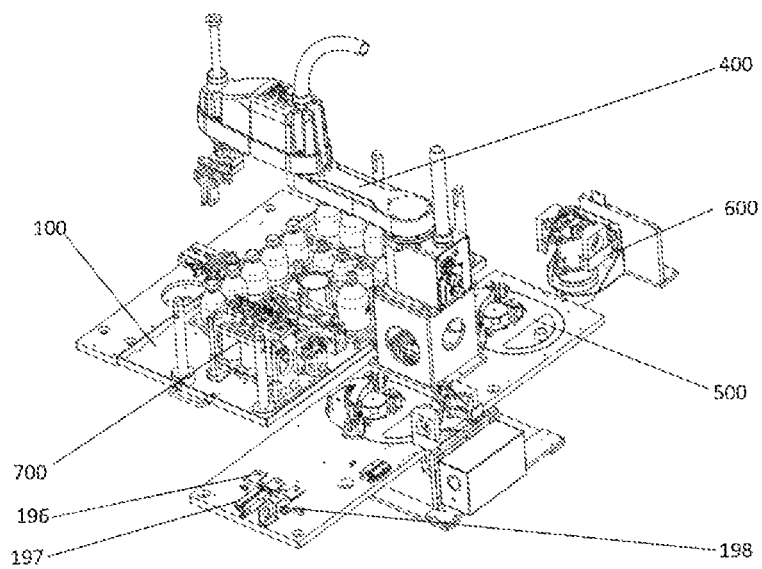
FIG. 1 is an overall structure view of an embodiment 1.
Figure 2:
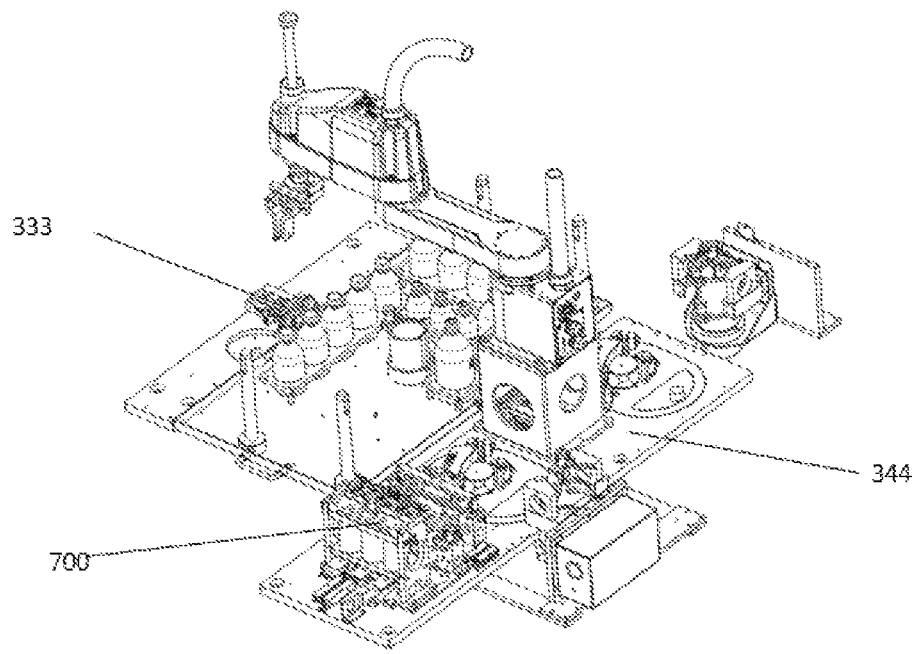
FIG. 2 is an overall structure view of the embodiment 1 during operating.

Embodiment 1: 250 ml and 100 ml multi-layer large-volume bottled aqueous solution test sample Referring to FIGS. 1-2, an intelligent bacteria collection system according to the embodiment 1 comprises: a guide rail (not shown), a first tray module 100, a manipulator module 400, a peristaltic pump module 500, a flipping mechanism module 600, and a control infusion module 700. The tray module 100 is placed on the guide rail; the peristaltic pump module 500 is provided on one side of the tray module 100, and a tray positioning device 333 is provided on the other side of the tray module 100; the manipulator module 400 and the peristaltic pump module 500 are fixed on an infusion operation platform 344; the control infusion module 700 is placed on the tray module 100, which is transported to by the manipulator module 400, and is fixed on the infusion operation platform 344 by a cylinder and a positioning pin.

The infusion operation platform 344 is equipped with a liquid outlet device; the liquid outlet device comprises a liquid outlet diversion tank 196, a feeding cylinder 197, and a waste liquid recovery tank 198; three holes are drilling on a top of the liquid outlet diversion tank 196, which are connected to liquid outlet ports of under-bottle pipes of three culture bottles; the liquid outlet diversion tank 196 has a hollow inside; gathered liquid flows out through a liquid outlet port at a bottom of the liquid outlet diversion tank 196, and the waste liquid recovery tank 198 is provided right below the liquid outlet port for recovering waste liquid; the feeding cylinder 197 is connected to and drives the liquid outlet diversion tank 196 to move forward and backward. The liquid outlet diversion tank 196 and the feed cylinder 197 are both placed on a bracket with a pre-set height, and the bracket is connected to the infusion operation platform 344 bolts to be fixed at a designated position. During liquid discharging, a lower cap stopper is opened, and the feeding cylinder 197 controls the liquid outlet diversion tank 196 to move forward to a position directly opposite to the liquid outlet port of the under-bottle pipe of the culture bottle, so that the waste liquid can flow into the waste liquid recovery tank 198 through the liquid outlet diversion tank 196.

Figure 3:
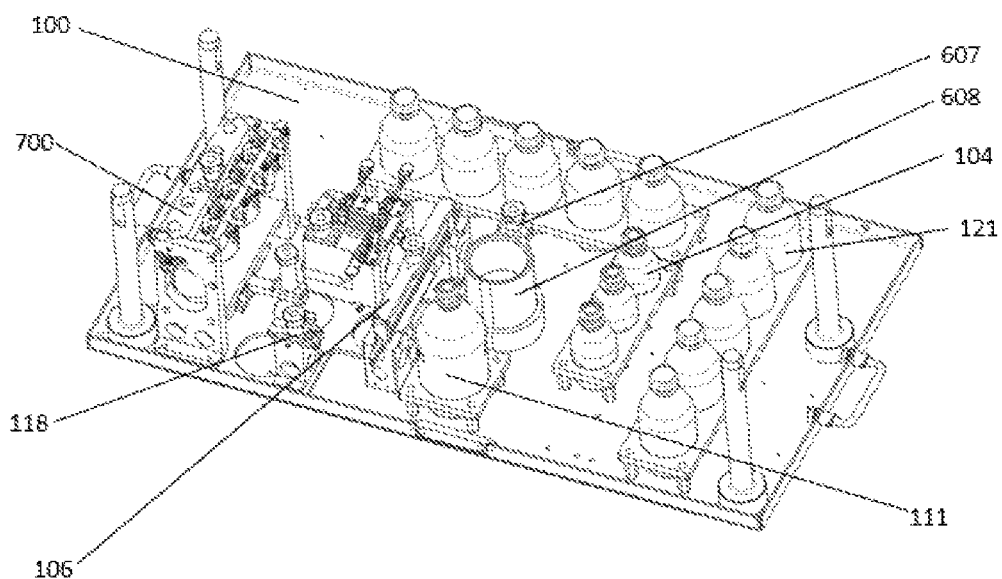
FIG. 3 is a structure view of a tray module in the embodiment 1.
Figure 4:
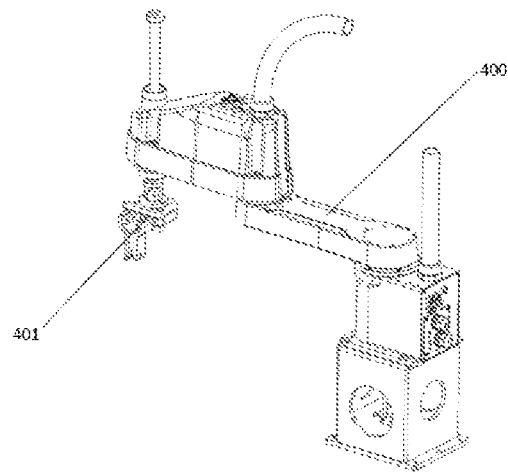
FIG. 4 is a structure view of a mechanical arm module.
Figure 5:
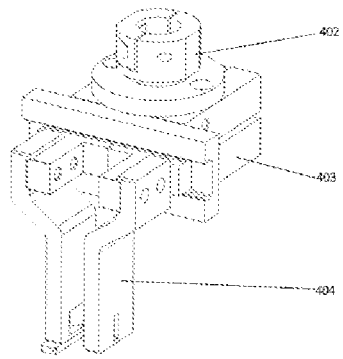
FIG. 5 is an enlarged view of a mechanical gripper in FIG. 4.

Referring to FIG. 3, the tray module 100 comprises: a tray, a moisturizing cleaning solution bottle 111, a culture medium bottle 104, a large-volume bottled aqueous solution test sample 121, a container adaptor 608, and the control infusion module 700 placed on the tray; wherein the container adaptor 608 is used to place small reagent bottle to facilitate grasping of a flipping mechanism; a first imitation bottle head 607 is provided on the container adaptor 608, and multiple imitation bottle heads are provided on the control infusion module 700. The manipulator module 400 clamps the imitation bottle heads on the control infusion module 700, and moves and places the infusion control module 700 of the first tray module 100 on the infusion operation platform 344, wherein the infusion control module 700 is fixed on the infusion operation platform 344 by the cylinders and the positioning pin. A hole is drilled on the tray, which cooperates with the tray positioning device 333 for positioning the first tray module 100. According to the embodiment 1, the tray positioning device 333 comprises the cylinder and the positioning pin, and the positioning pin is driven by the cylinder for positioning Referring to FIGS. 4 and 5, the manipulator module 400 comprises a mechanical arm and a mechanical gripper 401. In the embodiment 1, the mechanical arm of the manipulator module 400 is a four-axis mechanical arm (for example, a model LS6SCARA four-axis mechanical arm). The mechanical gripper 401 is used in conjunction with the bottle head or the imitation bottle head to grip the bottle head or the imitation bottle head in each module, so as to transport the corresponding module or structure to a designated position. The mechanical gripper 401 comprises a bearing connector 402, a sliding cylinder 403, and a bottle head holding part 404; the bearing connector 402 is connected to the mechanical arm; the sliding cylinder 403 drives the bottle head holding part 404 to loosen and fasten, so as to hold the bottle head or the imitation bottle head tightly.

Figure 6:
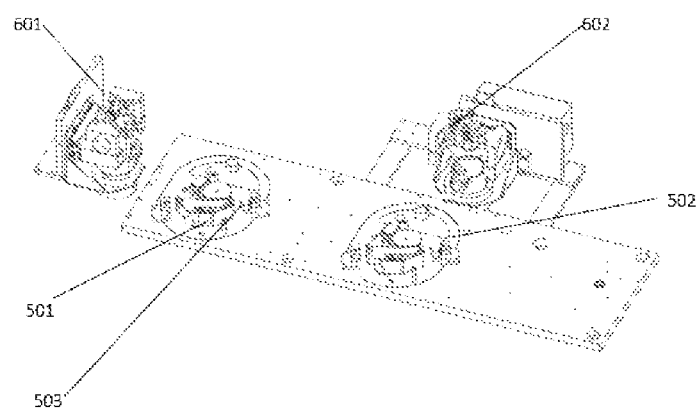
FIG. 6 is a structure view of relative positions of a peristaltic pump module and a flipping module.

Referring to FIG. 6, the peristaltic pump module 500 comprises two peristaltic pumps (only one of them is used in the embodiment 1): a first peristaltic pump 501 and a second peristaltic pump 502 (used in the embodiment 1); each of the peristaltic pumps has a hose mounting assembly installation slot 503; the flipping mechanism module 600 comprises two flipping mechanism (only one of them is used in the embodiment 1): a first flipping mechanism 601 and a second flipping mechanism 602 (used in the embodiment 1); the first flipping mechanism 601 is provided on one side of the first peristaltic pump 501, and the second flipping mechanism 602 is provided on one side of the second peristaltic pump 502; during operating, the first flipping mechanism 601 cooperates with the first peristaltic pump 501, and the second flipping mechanism 602 cooperates with the second peristaltic pump 502.

For convenience, the first flipping mechanism 601 and the first peristaltic pump 501 are provided on one side of the manipulator module 400, and the second flipping mechanism 602 and the second peristaltic pump 502 are provided on the other side of the manipulator module 400.

Figure 7:
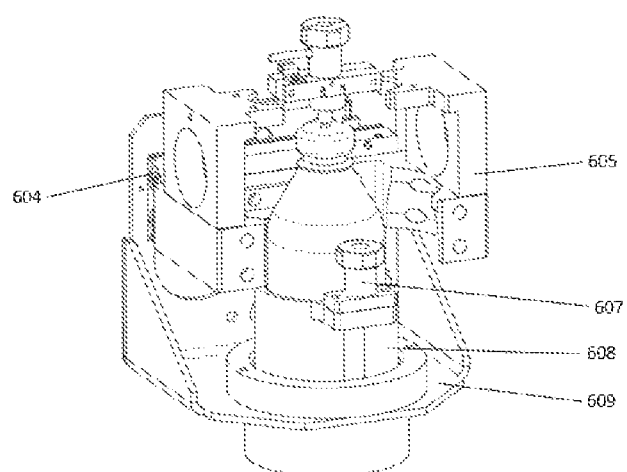
FIG. 7 is an enlarged view of the flipping module.

Referring to FIG. 7, each flipping mechanism comprises a sliding table 605, a sliding table cylinder 604, and a flipping base 609. The sliding table cylinder 604 drives the sliding table 605 to hold a test solution bottle. The sliding table 605 is arranged on the flipping base 609, and is connected to the sliding table cylinder 604; the sliding table cylinder 604 drives the sliding table 605 to open and close.

Figure 8:
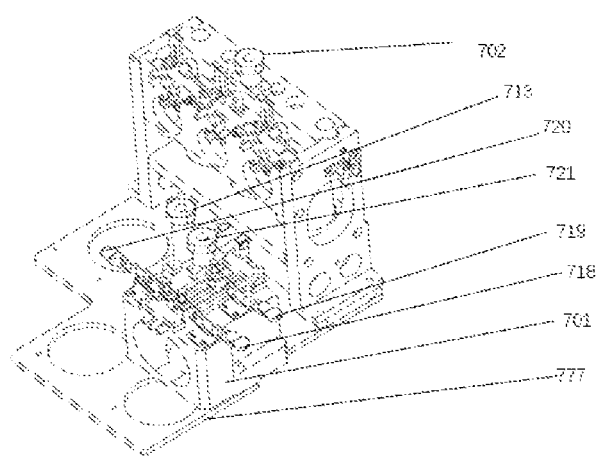
FIG. 8 is a right side view of a control infusion module.

Referring to FIG. 8, the control infusion module 700 comprises a first hose mounting assembly 106, a first needle 118, a fixed support plate 777, a tube fixing seat 701, a horizontal clamp, a culture device tooling, a tube clamp, a movable blade knife and the culture bottle; wherein the fixed support plate 777 fixes and supports all parts, so as to stabilize the entire control infusion and collection device. Quantities of the horizontal clamp, the culture device tooling, the tube clamp, the movable blade knife, and the culture bottle are identical and corresponding to each other, and are equal to a quantity of the infusion tubes in the first hose mounting assembly 106.

The first hose mounting assembly 106 comprises a hose clamp and one or more infusion tubes; the infusion tubes are fixed on the hose clamp, and one end of each of the infusion tubes is connected to the first needle 118 through a pipeline, and the other end of each of the infusion tubes is connected to a culture bottle inlet through the horizontal clamp, the tube clamp, and the movable blade knife in turn; a second imitation bottle head is provided on the first hose mounting assembly 106, and a third imitation bottle head is provided on the first needle 118, which facilitate gripping of the manipulator module 400.

The tube fixing seat 701 is used to install the horizontal clamp, to fix the infusion tubes in the first hose installation assembly 106, and to ensure that liquid conveyed in the infusion tubes is accurately and smoothly input into the culture bottle. The horizontal clamp acts as a switch for the infusion tube: when the infusion tube delivers liquid, the horizontal clamp is opened, and the liquid is delivered to the culture bottle through the infusion tube; when the liquid in the culture bottle is fully collected, the horizontal clamp is closed and the liquid delivery to the culture bottle is stopped. A fourth imitation bottle head 721 is provided on the fixed pressure tube base 701, which facilitate gripping of the manipulator module 400.

The culture device tooling comprises a first culture device tooling 714, a second culture device tooling 715, a third culture device tooling 716, and a fourth culture device tooling 717; the cap stopper fixing assembly is provided on a top of the culture device tooling. The first culture device tooling 714 and the second culture device tooling 715 are fixed on the fixed support plate 777, which fix left and right sides of the culture bottle and limit the cap stopper fixing assembly; the third culture device tooling 716 is mounted on middle top portions of the first culture device tooling 714 and the second culture device tooling 715, which fixes the top of the culture bottle, as well as limits and fixes the clamp tube and the movable blade knife, which facilitates subsequent cutting of the infusion tubes; the fourth culture device tooling 717 is mounted on middle portions of the first culture device tooling 714 and the culture device tooling 715, which fixes a middle of the culture bottle.

The movable blade knife is used to cut the pipeline between the infusion tube and the culture bottle. A right side of the movable blade knife is connected to a tension spring, and the mechanical arm pushes the movable blade knife cut the infusion tube. When the infusion tube is cut off, the mechanical arm returns, so that the movable blade knife returns to an initial position by a tension of the tension spring.

Figure 9:
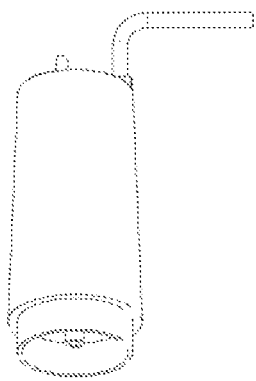
FIG. 9 is a structure view of a culture bottle in FIG. 8.

Referring to FIG. 9, an infusion tube installation hole and an upper cap stopper are arranged on a top of the culture bottle; an under-bottle pipe is arranged at a bottom of the culture bottle; a filter is provided inside the culture bottle; the culture bottle is used to collect bacteria in the input liquid sample; the culture bottle is placed in the culture device tooling to be fixed; the liquid in the culture bottle is discharged through the under-bottle pipe to the waste liquid recovery tank 198 of the liquid outlet device, and then the culture bottle collects the bacterial colony in the liquid sample delivered to the culture bottle through the infusion tube.

Figure 10:
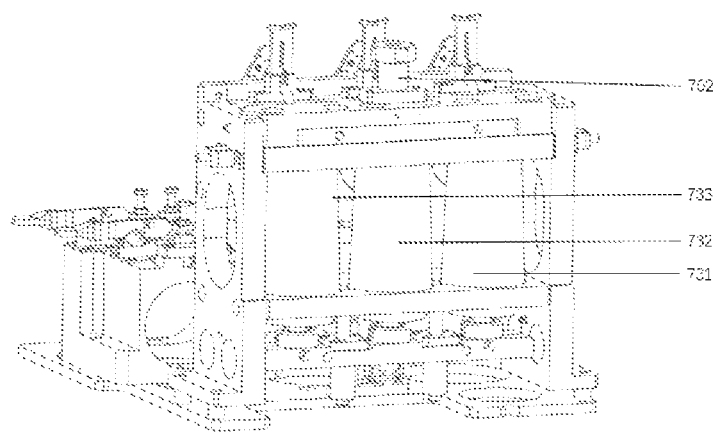
FIG. 10 is a rear view of the present invention.
Figure 11:
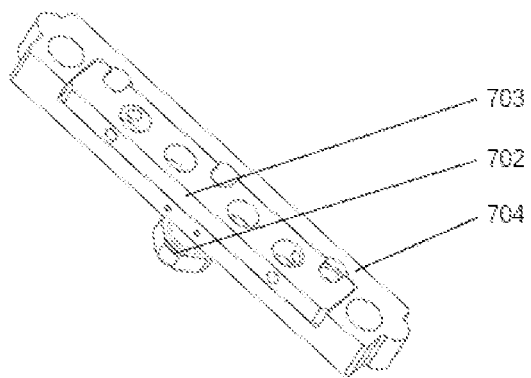
FIG. 11 is a structure view of a cap stopping fixing assembly in FIG. 8.

Referring to FIGS. 10 and 11, a fifth imitation bottle head 702 is provided on the cap stopper fixing assembly; the cap stopper fixing assembly comprises an upper cap stopper clamping plate 703 and an upper cap stopper fixing plate 704; cooperating holes are arranged between the upper cap stopper clamping plate 703 and the upper cap stopper fixing plate 704, for fixing the upper cap stopper of the culture bottle; tightness of the upper stopper cap can be adjusted by a tightness adjustment screw fixed on the upper cap stopper fixing plate 704. When the fifth imitation bottle head 702 is lifted up, the upper cap plug opens. When the fifth imitation bottle head 702 is pressed down, the upper cap plug is closed.

Figure 12:
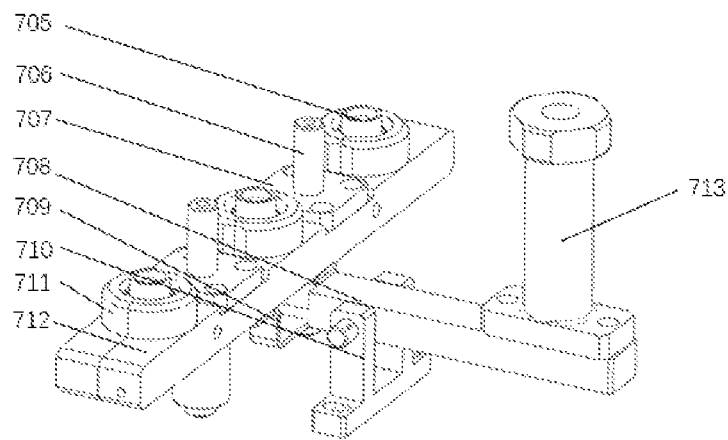
FIG. 12 is a structure view of an under-bottle pipe blocking assembly in FIG. 8.

Referring to FIG. 12, a sixth imitation bottle head 713 controls the under-bottle pipe blocking assembly of the culture bottle. The under-bottle pipe blocking assembly adopts a lever structure: when the sixth imitation bottle head 713 is lifted up, the under-bottle pipe blocking assembly opens; when the sixth imitation bottle head 713 is pressed down, the under-bottle pipe blocking assembly is closed.

The sixth imitation bottle head 713 is fixed on the under-bottle pipe blocking assembly; the under-bottle pipe blocking assembly comprises a lower cap stopper 705, a bare shaft 706, a linear bearing 707, a lever 708, a connecting piece 709, a bracket 710, a front splint 711, and a rear splint 712. The lower cap stopper 705 is clamped and fixed by the front splint 711 and the rear splint 712; the liquid outlet port of the under-bottle pipe is arranged opposite to the lower cap stopper 705; the front and rear splints are equipped with the linear bearing 707, and the linear bearing 707 is connected to the bare shaft 706, so that the splints are driven by the bare shaft to move up and down. The sixth imitation bottle head 713 is connected to the lever 708; the connecting piece 709 is provided under the front and rear splints. The splint assembly on the left is connected to the sixth imitation bottle head 713 on the right through the connecting piece 709; by pressing or pulling the sixth imitation bottle head 713, the splint assembly on the left can move up and down, so as to drive the lower cap stopper 705 to move up and down. As a result, the liquid flows out of the culture bottle through the lower cap stopper 705.

The tube clamp is a switch between the infusion tube and the culture bottle: when the bacteria collection is completed, the manipulator module 400 presses the tube clamp downwards to close the infusion tube, so as to prevent bacteria in the air from entering the culture bottle.

Figure 13:
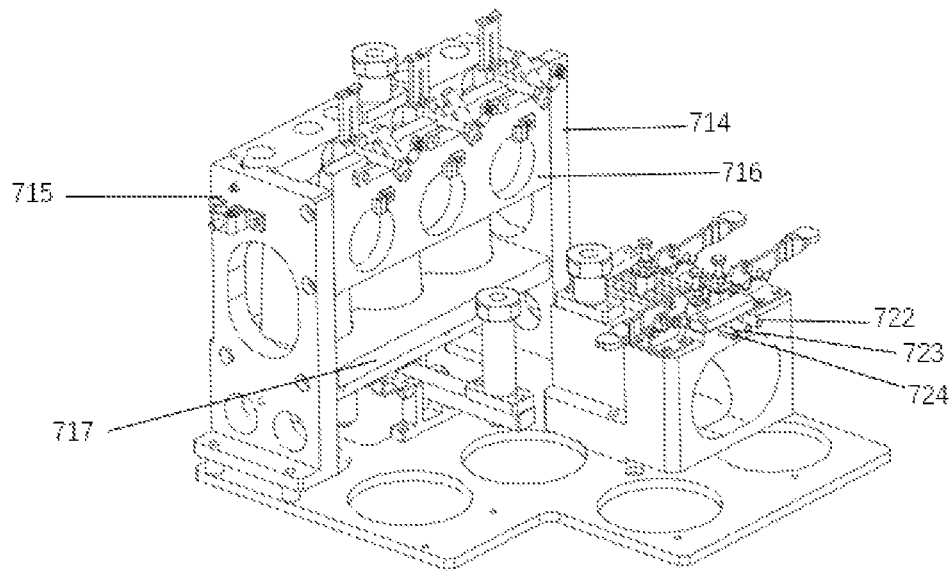
FIG. 13 is a left side view of the control infusion module.

Referring to FIG. 13, in the embodiment 1, the control infusion module 700 has three horizontal clamps, three tube clamps, and three culture bottles. Correspondingly, the first hose mounting assembly 106 has three infusion tubes, which are connected to a first infusion tube 722, a second infusion tube 723, and a third infusion tube 724 of the control infusion module 700, respectively. A first horizontal clamp 718, a second horizontal clamp 719, and a third horizontal clamp 720 are installed on the tube fixing seat 701, so as to fix the first infusion tube 722, the second infusion tube 723, and the third infusion tube 724, thereby ensuring that the liquid transported in the tube can be accurately and smoothly input into a first culture bottle 731, a second culture bottle 732, and a third culture bottle 733. The first infusion tube 722, the second infusion tube 723, and the third infusion tube 724 ensure that the liquid transported in the tube (under the action of the peristaltic pump) can be smoothly input into the culture bottles.

The first culture bottle 731, the second culture bottle 732, and the third culture bottle 733 are all placed in the culture device tooling. The first culture bottle 731 is used to store the liquid delivered by the first infusion tube 722. After the liquid in the first culture bottle 731 is discharged through the under-bottle pipe, the first culture bottle 731 collects the bacteria in the liquid delivered therein through the first infusion tube 722. The second culture bottle 732 collects the bacteria in the liquid delivered therein through the second infusion tube 723. The third culture bottle 733 collects the bacteria in the liquid delivered therein through the third infusion tube 724.

The fifth imitation bottle head 702 functions as a switch for the upper cap stoppers of the first culture bottle 731, the second culture bottle 732, and the third culture bottle 733. The sixth imitation bottle head 713 functions as a switch for the under-bottle pipes of the first culture bottle 731, the second culture bottle 732, and the third culture bottle 733.

Figure 14:
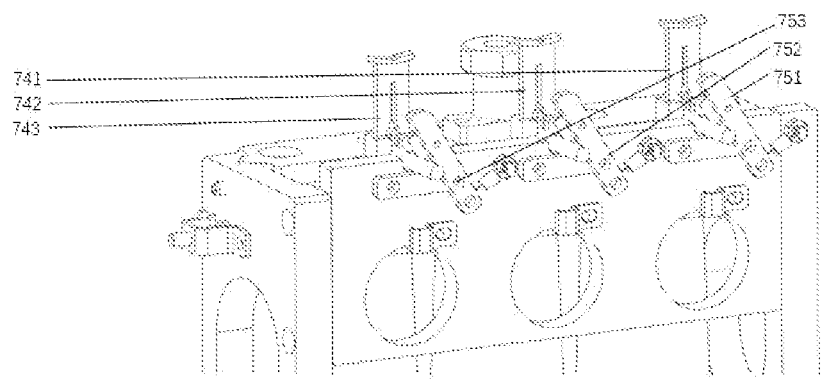
FIG. 14 is a structure view of a movable blade knife module in FIG. 13.

As shown in FIG. 14, the first tube clamp 741 is a switch between the first infusion tube 722 and the first culture bottle 731. The second tube clamp 742 is a switch between the second infusion tube 723 and the second culture bottle 732. The third tube clamp 743 is a switch between the third infusion tube 724 and the third culture bottle 733.

A first movable blade knife 751 is used to cut the infusion tube connected between the first infusion tube 722 and the first culture bottle 731. A second movable blade knife 752 is used to cut the infusion tube connected between the second infusion tube 723 and the second culture bottle 732. A third movable blade knife 753 is used to cut the infusion tube connected between the third infusion tube 724 and the third culture bottle 733.

Operation process of the embodiment 1 is as follows:

An initial state of the control infusion module 700 is: the upper cap stopper blocks the hole on the top of the culture bottle, and the lower cap stopper 705 blocks the liquid outlet port at the bottom of the culture bottle; and the three horizontal clamps are all opened.

Step 1. Washing the culture bottle:

The mechanical gripper 401 clamps the fourth imitation bottle head 721 to move the control infusion module 700 on the tray to the control infusion operation platform 344, and fix the control infusion module 700 on the infusion operation platform 344 through the cylinder and the positioning pins. At this time, the liquid output device is located on a side of the liquid outlet port at the bottom of the culture bottle in the control infusion module 700;

then the mechanical gripper 401 grips and moves the moisturizing cleaning solution bottle 111 on the tray, and places it in the second flipping mechanism 602; the second flipping mechanism 602 holds the bottle body tightly;

then the mechanical gripper 401 grips and moves the first hose mounting assembly 106 to the hose mounting assembly installation slot 503 of the second peristaltic pump 502;

then the mechanical gripper 401 lifts the fifth imitation bottle head 702 upward to open the liquid inlet on the top of the culture bottle;

then the mechanical gripper 401 grips and moves the first needle 118, so as to insert the first needle 118 into the moisturizing cleaning solution bottle 111. The second flipping mechanism 602 turns the moisturizing cleaning solution bottle 111 upside down, and the second peristaltic pump 502 is turned on to transfer a moisturizing cleaning solution to the culture bottle of the control infusion module 700, thereby moisturizing a microporous filter membrane in the culture bottle; when the moisturizing cleaning solution reaches a pre-set injection volume, the second peristaltic pump 502 is turned off.

Then the manipulator module 400 pushes the fifth imitation bottle head 702 downwards to close the liquid inlet on the top of the culture bottle; and the manipulator module 400 lifts the sixth imitation bottle head 713 upwards to open the liquid outlet port at the bottom of the culture bottle; the feeding cylinder 197 is turned on to drive the liquid outlet diversion tank 196 to move horizontally, so that the three holes on the top of the liquid outlet diversion tank 196 are connected to the liquid outlet ports at the bottoms of the three culture bottles (the liquid outlet ports of the under-bottle pipes); the flipping mechanism 602 turns the moisturizing cleaning solution bottle 111 upright, and the second peristaltic pump 502 is turned on to pump gas into the culture bottle for pressurization, so that the moisturizing cleaning solution is completely discharged from the under-bottle pipes of the three culture bottles to the waste liquid recovery tank 198 of the liquid discharge device; the peristaltic pump 502 is turned off after the moisturizing cleaning solution is completely discharged;

the manipulator module 400 lifts the fifth imitation bottle head 702 upward to open the liquid inlet on the top of the culture bottle; and the manipulator module 400 pushes the sixth imitation bottle head 713 downward to close the liquid outlet port at the bottom of the culture bottle;

then the manipulator module 400 pulls out the first needle 118 from the moisturizing cleaning solution bottle 111 and puts it back into the control infusion module 700. The manipulator module 400 grips and moves the moisturizing cleaning solution bottle 111 to the tray to complete washing the culture bottle.

Step 2. Transferring and filtering of the large-volume bottled aqueous solution test sample:

The manipulator module 400 grips and moves the large-volume bottled aqueous solution test sample 121 in the tray, and puts the large-volume bottled aqueous solution test sample 121 into the second flipping mechanism 602; a transfer process of the large-volume bottled aqueous solution is the same as the transfer process of the moisturizing cleaning solution to the culture bottle, except that the moisturizing cleaning solution bottle is replaced with the large-volume bottle.

Step 3. Transferring a medium in the medium bottle 104 to the culture bottle:

The manipulator module 400 grips and moves the container adaptor 608 in the tray to the flipping mechanism 602, and then grips and moves the culture medium bottle containing the medium in the tray into the flipping mechanism 602, and holds it tightly for positioning;

then the manipulator module 400 grips and moves the first needle 118 in the control infusion module 700, and inserts the first needle 118 into the culture medium bottle containing the medium; the manipulator module 400 presses the second horizontal clamp 719 and the third horizontal clamp 720 to block the second infusion tube 723 and the third infusion tube 724, so as to prevent the medium in the culture bottle from flowing-in; the flipping mechanism module 600 turns the culture bottle upside down, and the peristaltic pump 502 is turned on to pump the medium into the first culture bottle 731; when the medium reaches a pre-set injection volume, the peristaltic pump 502 is turned off; then the flipping mechanism module 600 turns the culture medium bottle upright, and the manipulator module 400 pulls out the first needle in the culture medium bottle and puts it back to an original location; and the manipulator module 400 grips and moves the culture medium bottle to the tray.

Then the manipulator module 400 grips and moves another culture medium bottle containing the medium in the tray into the flipping mechanism 602, and holds it tightly; the manipulator module 400 grips and moves the first needle 118, and inserts the first needle into the culture medium bottle; the manipulator module 400 presses the first horizontal clamp 719, pulls the second horizontal clamp 719, opens the second infusion tube 723, and repeats the same medium pumping process as that of the first culture bottle 731; the manipulator module 400 grips and moves yet another culture medium bottle in the tray into the flipping mechanism 602, and holds it tightly; the manipulator module 400 grips and moves the first needle 118, and inserts the first needle into the culture medium bottle; the manipulator module 400 presses the second horizontal clamp 719, pulls the third horizontal clamp 720, opens the third infusion tube 724, and repeats the same medium pumping process; when the medium in the third culture bottle reaches a pre-set injection volume, the mechanical arm presses the third horizontal clamp 720 to close it; the manipulator module 400 grips and moves the container adaptor 608 and puts it back on the tray;

at this time, the three horizontal clamps are all closed for tightly pressing the three infusion tubes;

Step 4. completing the bacteria collection:

The manipulator module 400 grips and moves the first hose mounting assembly 106 to the control infusion module 700; the manipulator module 400 pushes the fifth bottle head 702 downwards to close the liquid inlet on the top of the culture bottle; the manipulator module 400 presses the first tube clamp 741, the second tube clamp 742, and the third tube clamp 743 of the control infusion module 700 into a fixing groove to clamp the infusion tube connected to the culture bottle; then the manipulator module 400 presses the first movable blade knife 751, the second movable blade knife 752, and the third movable blade knife to cut off the three infusion tubes. Then the control infusion module 700 placed on the infusion operation platform 344 is unlocked, and the manipulator module 400 grips and moves the control infusion module 700 back to the tray.

The guide rail transports the first tray module 100 out of a bacteria collection operation area, and the next tray module enters the bacteria collection operation area for the next bacteria collection.

Embodiment 2: 10 ml ampoule bottled aqueous solution test sample

Figure 15:
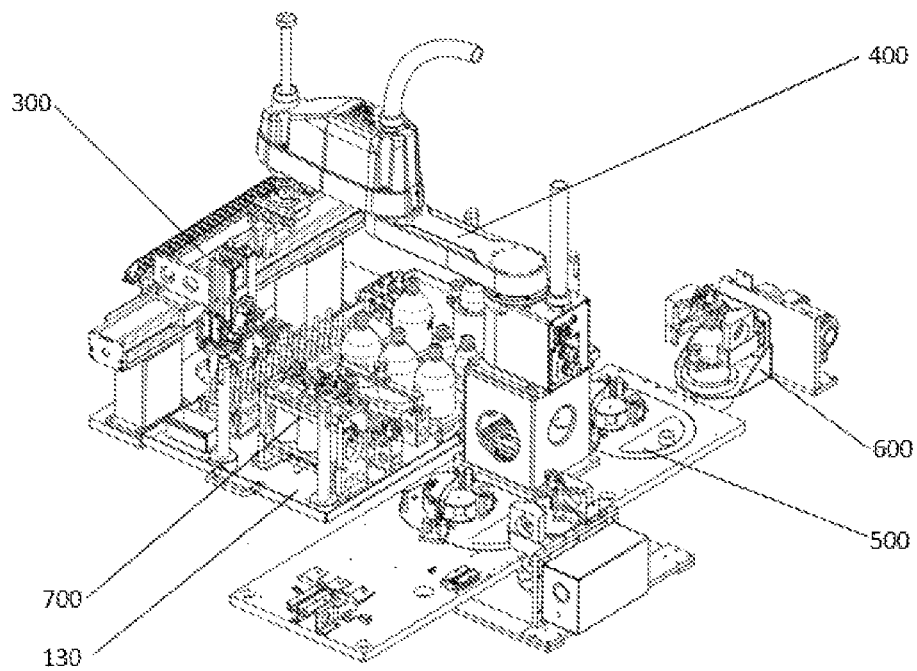
FIG. 15 is an overall structure view of an embodiment 2.
Figure 16:
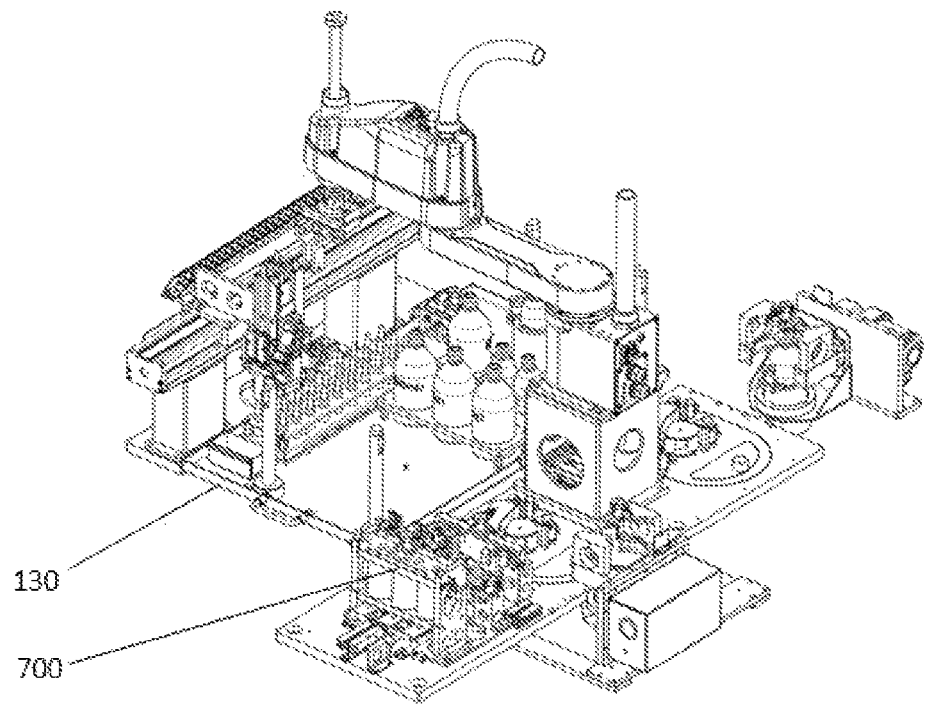
FIG. 16 is an overall structure view of the embodiment 2 during operating.

Referring to FIGS. 15 and 16, the intelligent bacteria collection system according to the embodiment 2 comprises: a second tray module 130, a bottle opening module 300, a manipulator module 400, a peristaltic pump module 500, a flipping mechanism module 600, and a control infusion module 700.

The bottle opening module 300 is arranged opposite to the peristaltic pump module 500, a guide rail is arranged between the bottle opening module 300 and the peristaltic pump module 500, and the second tray module 130 is placed on the guide rail; the bottle opening module 300 is fixed by a bottle opening module fixing plate; the manipulator module 400 and the peristaltic pump module 500 are fixed on the infusion operation platform 344. The control infusion module 700 is placed on a tray module 100 and can be moved to the infusion operation platform 344 through the manipulator module 400; the infusion operation platform 344 is fixed by a cylinder and a positioning pin.

The difference between the embodiment 2 and the embodiment 1 is that the composition of the tray module is different, and the embodiment 2 further comprises the bottle opening module 300.

Figure 17:
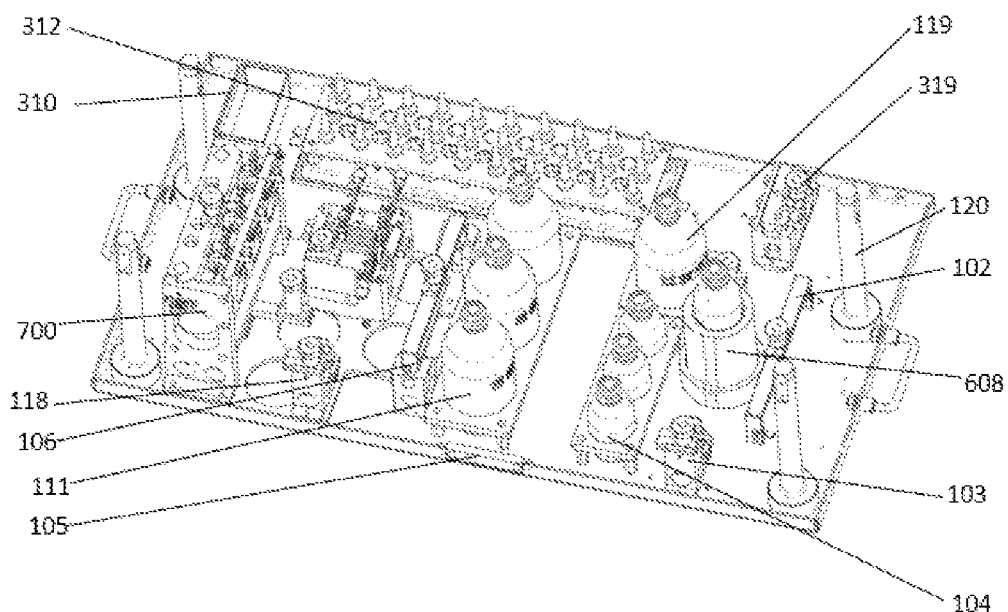
FIG. 17 is a structure view of a tray module in the embodiment 2.

Referring to FIG. 17, the second tray module 130 comprises a tray, an ampoule assembly (comprising an ampoule 312 and an ampoule fixing plate 313), a discharging groove 310, the control infusion module 700, a moisturizing cleaning solution bottle 111, a transition bottle 119, and a three-needle tooling 319, tray support rods 120, a second needle 103, a second hose mounting assembly 102, and a culture medium bottle 104.

In the embodiment 2, the transition bottle 119 is an empty bottle for transitioning an ampoule liquid into a bacteria collection bottle.

The ampoule assembly and the discharging groove 310 are placed on a side near the bottle opening module 300 to facilitate the opening of the bottle opening module 300 and the discharging of the bottle head. The tray support rods 120 are provided at the four corners of the tray for stacking multiple trays, which is convenient for transportation.

The second hose mounting assembly 102 has the same structure as the first hose mounting assembly 106, which comprises a hose clamp and one or more infusion tubes; the infusion tubes are fixed on the hose clamp, and one end of each of the infusion tubes is connected to the second needle 103 through a pipeline, and the other end of each of the infusion tubes is connected to a liquid outlet of the three-needle tooling 319 for sucking the test sample into the transition bottle.

Figure 18:
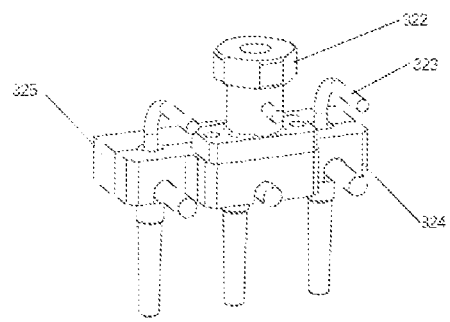
FIG. 18 is a structure view of a three-needle tooling in FIG. 17.

Referring to FIG. 18, the three-needle tooling 319 comprises a first needle clamping jaw 324, a second needle clamping jaw 325, three needles 323, and a seventh imitation bottle head 322. The first needle clamping jaw 324 and the second needle clamping jaw 325 clamp the three needles 323 to form a liquid suction device. The seventh imitation bottle head 322 is provided on the first needle clamping jaw 324 to facilitate gripping of the manipulator module 400.

Figure 19:
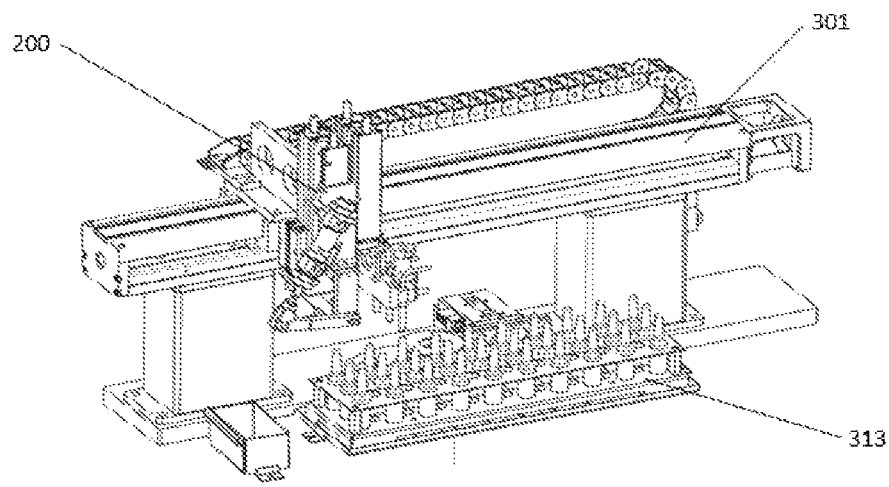
FIG. 19 is an overall structure of a bottle opening module in the embodiment 2.
Figure 22:
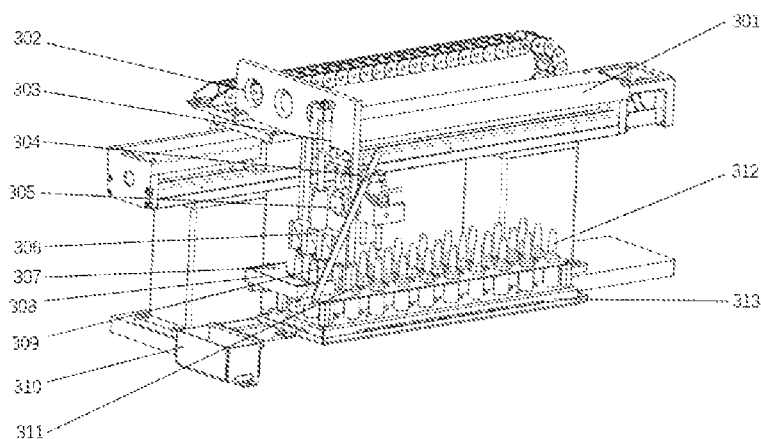
FIG. 22 is a front overall structure of an alternative bottle opening module in the embodiment 2.

Referring to FIGS. 19 and 22, there are two types of bottle opening module 300 in the embodiment 2.

Figure 20:
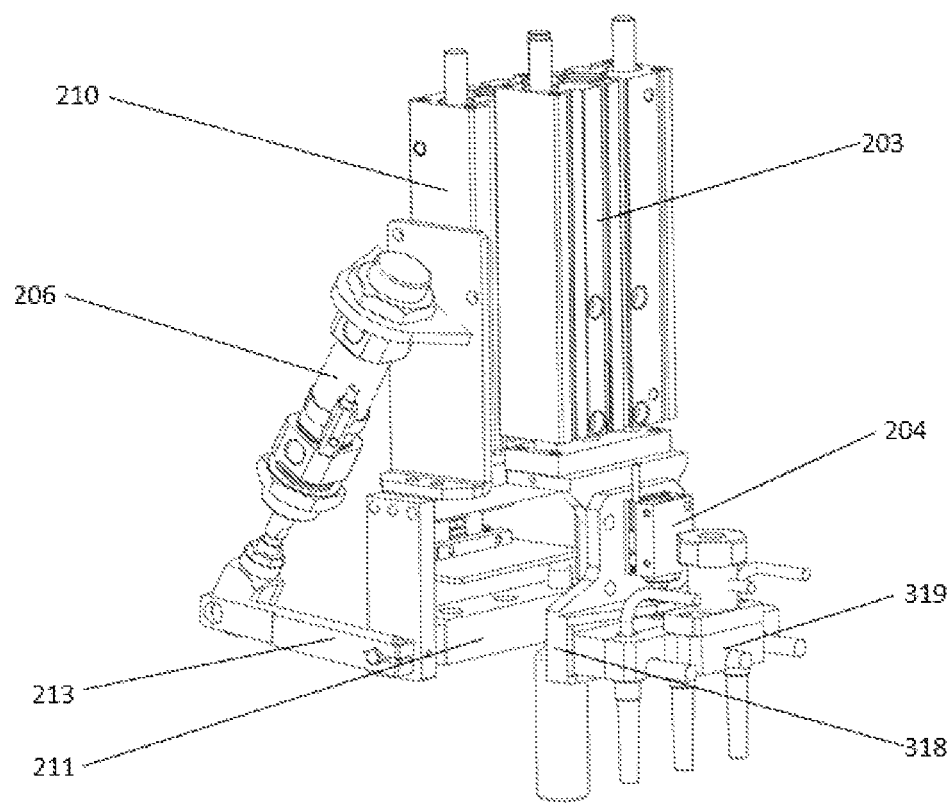
FIG. 20 is a partial enlarged view of FIG. 19.
Figure 21:
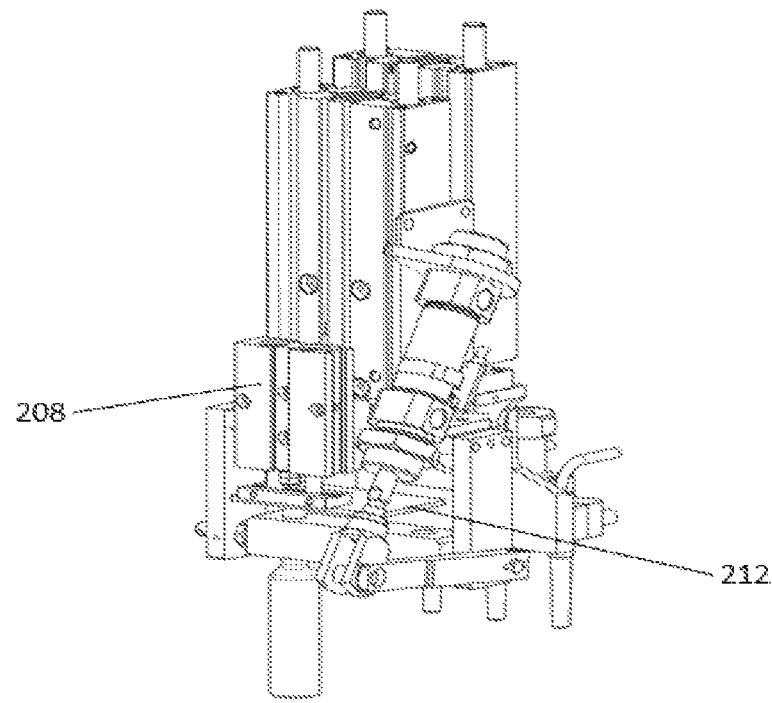
FIG. 21 is another partial enlarged view of FIG. 19.

Referring to FIGS. 19-21, the bottle opening module comprises a linear module 301 (Shanghai Silver KK86-740A1 ball screw linear slide is used in the embodiment 2), a bottle opening lifting cylinder 210, a liquid pumping lifting cylinder 203, a bottle head nesting plate 211, a breaking plate 213, a top cover plate 212, a top cover cylinder 208, a bottle opening breaking cylinder 206, the needle mounting plate 318, and a pin cylinder 204.

The bottle opening lifting cylinder 210 and the liquid pumping lifting cylinder 206 are connected to and driven by the linear module 301 to move horizontally; the bottle opening lifting cylinder 210 is connected to and drives the bottle head nesting plate 211 to move vertically; the top cover plate 212 is arranged above the bottle head nesting plate 211, and is connected to and driven by the top cover cylinder 208 to move horizontally; the top cover plate 212 and the top cover cylinder 208 are both set on the bottle opening lifting cylinder 210 to move with the bottle head nesting plate 211; the bottle head nesting plate 211 is connected to and driven by the bottle opening breaking cylinder 210 through the breaking plate 213, so as to move horizontally; the liquid pumping lifting cylinder 203 is connected to and drives the needle mounting plate 318 to move vertically; the pin cylinder 204 and a clip slot are arranged on the needle mounting plate 318, which are matched with mounting holes of the three-needle tooling 319 to fix the three-needle tooling 319; a bottle head nesting hole is drilled on the bottle head nesting plate 211, and a rubber band is placed in the bottle head nesting hole.

During operating, the manipulator module 400 clamps the three-needle tooling 319 to the needle mounting plate 318, and the pin cylinder 204 cooperates with the clip slot to fix the three-needle tooling 319; the linear module 301 drives the entire bottle opening mechanism to move, so that the bottle head nesting plate 211 is above a first row of the ampoules; then the bottle opening lifting cylinder 210 moves downwards, and the bottle head nesting plate 211 nests the first row of the ampoules; the bottle opening breaking cylinder 206 drives the bottle head nesting plate 211 to break the ampoules. The bottle heads are stuck by the rubber ring in the bottle head nesting plate 211; the linear module 301 moves the three needles to a position above the opened ampoules, then the liquid pumping lifting cylinder 203 moves downwards, and the needles on the three-needle tooling 319 enters the ampoule to take out the test sample. Then the linear module 301 sends the bottle head nesting plate 211 with the bottle heads of the ampoules to a position above the discharging groove 310, and the top cover cylinder 208 drives the top cover plate 212 to move downwards, thereby pressing the bottle heads down to the discharging groove 310; then the linear module 301 drives the entire bottle opening mechanism to a position above a next row of the ampoules to repeat the bottle opening and pumping process.

Figure 23:
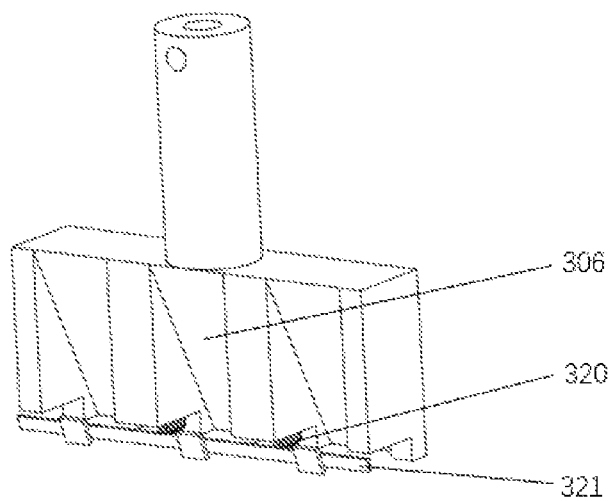
FIG. 23 is a structure of an inclined plane breaking plate in FIG. 21.
Figure 24:
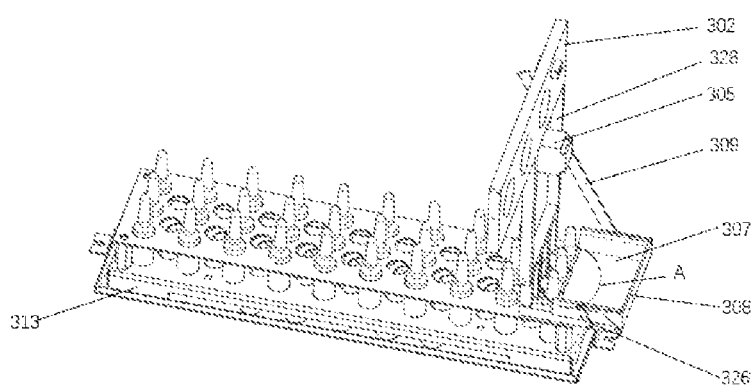
FIG. 24 is a structure of a discharging device in FIG. 21.

Referring to FIGS. 22-24, an alternative bottle opening module comprises a body, a linear module 301, a bottle opening device, a discharging device, and a liquid pumping device; the linear module 301, the bottle opening device, the discharging device and the liquid pumping device are all arranged on the body; the linear module 301 is arranged on a top of the body, and is connected to the bottle opening device, the discharging device and the liquid pumping device through a module adapter plate 302; the module adapter plate 302 is connected to a connecting plate on the linear module 301 through bolts; the bottle opening device and the discharging device are arranged on one side of the module adapter plate 302, and the liquid pumping device is arranged on the other side of the module adapter plate 302; during operating, a discharge side of the bottle opening device is arranged opposite to an inlet side of the discharging device.

In the embodiment 2, the linear module 301 is a Shanghai Silver KK86-740A1 ball screw linear slide, which drives the bottle opening device, the discharging device and the liquid pumping device to move horizontally;

the bottle opening device comprises a first push rod motor 303, an inclined breaking plate 306, and a spring push rod 321; the first push rod motor 303 is fixed on the one side of the module adapter plate 302, and the inclined breaking plate 306 is fixed on an output shaft of the first push rod motor 303, in such a manner that the first push rod motor 303 drives the inclined breaking plate 306 to move vertically, thereby breaking the bottle head of the ampoule 312.

Boards are provided at a middle and both sides of the inclined breaking plate 306 to prevent the broken ampoule bottle head from tipping after being disconnected. A spring push rod 321 is installed under the inclined breaking plate 306, and a spring 320 is installed in the spring push rod 321. The spring push rod 321 pushes the ampoule bottle head into a discharging plate 307 ahead at the moment when the ampoule bottle head is disconnected.

Figure 25:
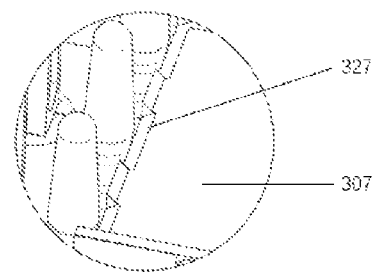
FIG. 25 is an enlarged view at A in FIG. 23.

Referring to FIG. 24, the discharging device comprises an ampoule adapter plate 311, a discharging plate 307, a rear baffle 308, a short connecting rod 326, a long connecting rod 309, a slider 304, a slider connecting rod 317 (see FIG. 25), and a rotating motor 305; wherein the ampoule adapter plate 311 is arranged at a bottom of the module adapter plate 302; in the embodiment 2, the ampoule adapter plate 311 is connected to an edge of the module adapter plate 302 by bolts, and the ampoule adapter plate 311 is tangent to a top surface of the ampoule fixing plate 313; the ampoule adapter plate 311 is driven by the linear module 301 to move horizontally, so as to break each row of the ampoules separately. Referring to FIG. 25, a front surface the discharging plate 307 has an inclined top corner 327 obliquing downwardly, which is used to withstand a bottleneck of the ampoule bottle, so as to cooperate with the inclined breaking plate to break the head of the ampoule bottle.

The discharging plate 307 is fixed on the ampoule adapter plate 311, and the rear baffle 308 is set on a discharge side of the discharging plate 307 through the short connecting rod 326 and long connecting rod 309 arranged on both sides of the discharging plate 307; the rear baffle 308 can rotate around an installation point; one end of the long connecting rod 309 is fixed with the ampoule adapter plate 311, the other end of the long connecting rod 309 is provided with the slider 304, and the slider 304 is connected to an output shaft of the rotating motor 305 through the slider connecting rod 317; the rotating motor 305 is fixed on a lateral extension plate 328 connected to the module adapter plate 302.

Figure 26:
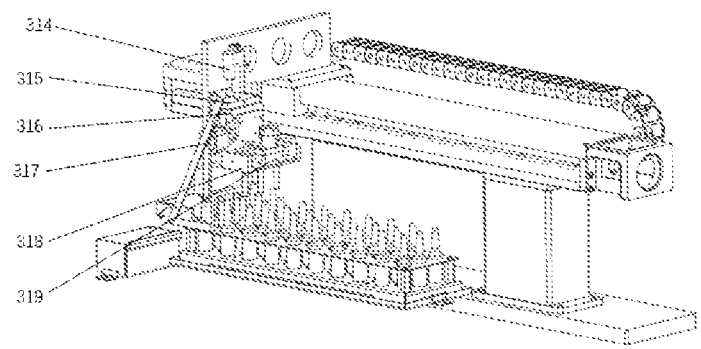
FIG. 26 is a reverse overall structure of the alternative bottle opening module in the embodiment 2.

Referring to FIG. 26, the pumping device comprises a second push rod motor 314, an intermediate connecting plate 315, a suction needle adapter 316, and the needle mounting plate 318. According to the embodiment 2, a connecting order of the above elements from top to bottom is that: the second push rod motor 314 is arranged on the other side of the module adapter plate 302; the intermediate connecting plate 315 is fixed on an output shaft of the second push rod motor 314, and is connected to the suction needle adapter 316; the needle mounting plate 318 is also connected to the suction needle adapter 316.

During operating, the manipulator module 400 grips the imitation bottle head 322 of the three-needle tooling 319, sends it to a position above the needle mounting plate 318, and then moves it to the clip slot of the needle mounting plate 318. At the same time, the three-needle tooling 319 is clamped tightly by fixing screws on both sides thereof. The linear module 301 drives the entire bottle opening mechanism to move, so that the inclined breaking plate 306 reaches a position above the first row of the ampoules, the push rod of the first push rod motor 303 moves downwards to lower the inclined breaking plate 306; a front top corner of the discharging plate 307 presses against a weakest position of the bottleneck of the first row of the ampoules, and breaks the heads of the first row of the ampoules through interaction with the inclined breaking plate 306. After the heads of the ampoules are pushed into the discharging plate 307 by the spring push rod 321, the linear module 301 moves to as position above the discharging groove 310. The rotating motor 305 rotates the slider connecting plate 317; the slider 304 is connected to the slider connecting plate 317; and the slider 304 is connected to the long connecting rod 309, wherein the slider 304 enables the long connecting rod 309 to swing around an installation point. The long connecting rod 309 is connected to the ampoule adapter plate 311 and the rear baffle 308, and the connection points are connected by cylindrical pins. The long connecting rod 309, the discharging plate 307, the rear baffle 308, and the ampoule fixing plate 311 form a turning mechanism. The cylindrical pin top and the ampoule adapter plate 311 together form a flipping mechanism, and the cylindrical pins and the ampoule adapter plate 311 form a fixed hinge point; the long connecting rod 309 is driven by the rotating motor 305 to rotate left and right around the fixed hinge point, so as to use the long connecting rod 309 as an active rod of the flipping mechanism. The long connecting rod and the rear baffle are connected by the cylindrical pin, and the rotation of the long connecting rod 309 drives the rear baffle 308 to move forward; the rear baffle 308 and the discharging plate 307 are connected by the cylindrical pin, and the discharging plate 307 is also connected to the ampoule adapter plate 311, in such a manner that the rear baffle 308 drives the discharging plate 307 to rotate around the cylindrical pin connected to the ampoule adapter plate 311, thereby pouring the ampoule bottle heads into the discharging groove 310. The linear module 301 drives the entire bottle opening mechanism to move, so that the three needles are located above the opened ampoules; the second push rod motor 314 moves downwards to push the push rod downward, thereby move the three-needle tooling 319 into the broken ampoules to take out the test sample. A next row of the ampoules can be opened and pumped by repeating the above process.

Operation process of the embodiment 2 is as follows:

An initial state of the control infusion module 700 is: the upper cap stopper blocks the hole on the top of the culture bottle, and the lower cap stopper 705 blocks the liquid outlet port at the bottom of the culture bottle; and the three horizontal clamps are all opened.

Step 1. Washing the culture bottle: which is the same as that of the embodiment 1.

Step 2. Transferring the test sample in the ampoules into the transition bottle:

the bottle opening module 300 opens all ampoules containing the aqueous solution test sample, and throws the discarded bottle heads into the discharging groove 310; the manipulator module 400 grips and moves the empty transition bottle 119 on the tray, places it in the flipping mechanism 601, and holds it tightly; the manipulator module 400 grips and moves the second hose mounting assembly 102 and places it in the hose mounting assembly installation slot of the first peristaltic pump 501; the mechanical arm clamps and moves the three-needle tooling 319 in the module to fix it with the needle mounting plate 318. The mechanical arm grips and moves the second needle 103 in the tray and inserts it into the transition bottle 119. The second push rod motor 314 moves the push rod downwards to insert the second needle 103 into a set of the ampoules containing the aqueous solution test sample; at the same time, the peristaltic pump 501 is turned on to transfer the aqueous solution test sample in the ampoules to the transition bottle 119; then the second push rod motor 314 moves the push rod upwards to pull out the second needle 103, and the linear module 301 drives the three-needle tooling 319 to a position above a next set of the ampoules containing the aqueous solution test sample to insert the needle into the ampoules and transfer the aqueous solution test sample in the ampoules to the transition bottle; the aqueous solution test sample in all the ampoules can be transferred to the transition bottle by repeating the above process, and then the first peristaltic pump 501 is turned off;

then the manipulator module 400 sequentially grips and moves the three-needle tooling 319, the second needle 103, and the transition bottle 119 to the original position on the tray.

Step 3. Transferring the test sample in the transition bottle 119 to the culture bottle of the control infusion module 700: which is the same as that of transferring the moisturizing cleaning solution to the culture bottle, except that the moisturizing cleaning solution bottle is replaced with the transition bottle.

Step 4. Transferring a medium in the medium bottle 104 to the culture bottle: which is the same as that of the embodiment 1.

Step 5. completing the bacteria collection: which is the same as that of the embodiment 1.

Embodiment 3: 10 ml vial bottled water-soluble solid test sample

Figure 27:
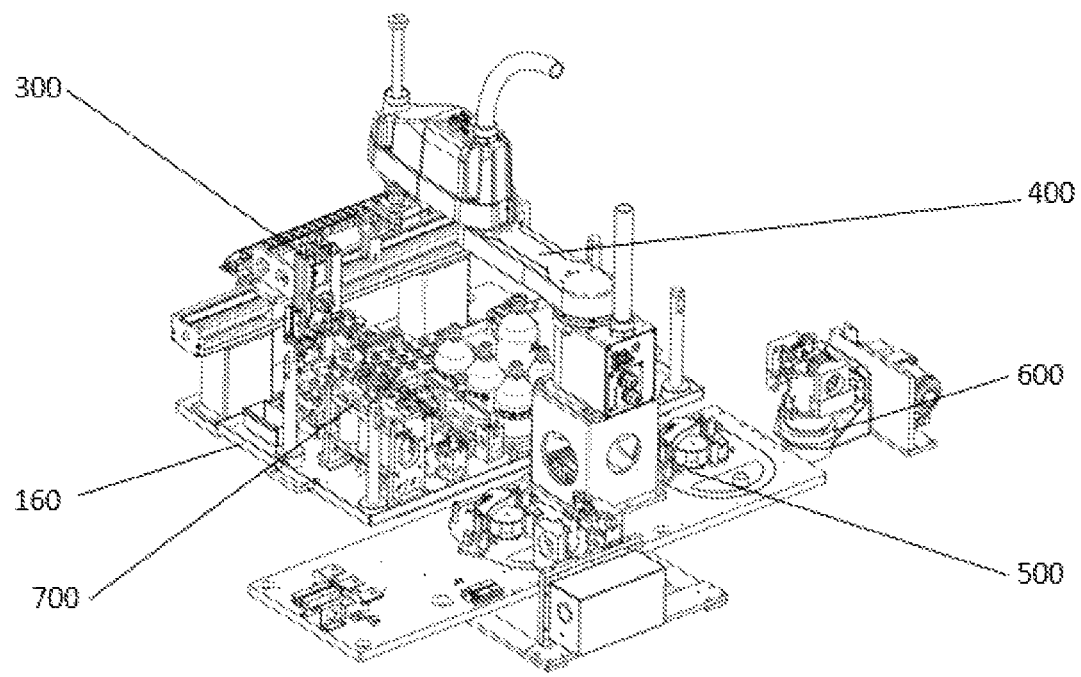
FIG. 27 is an overall structure view of an embodiment 3.
Figure 28:
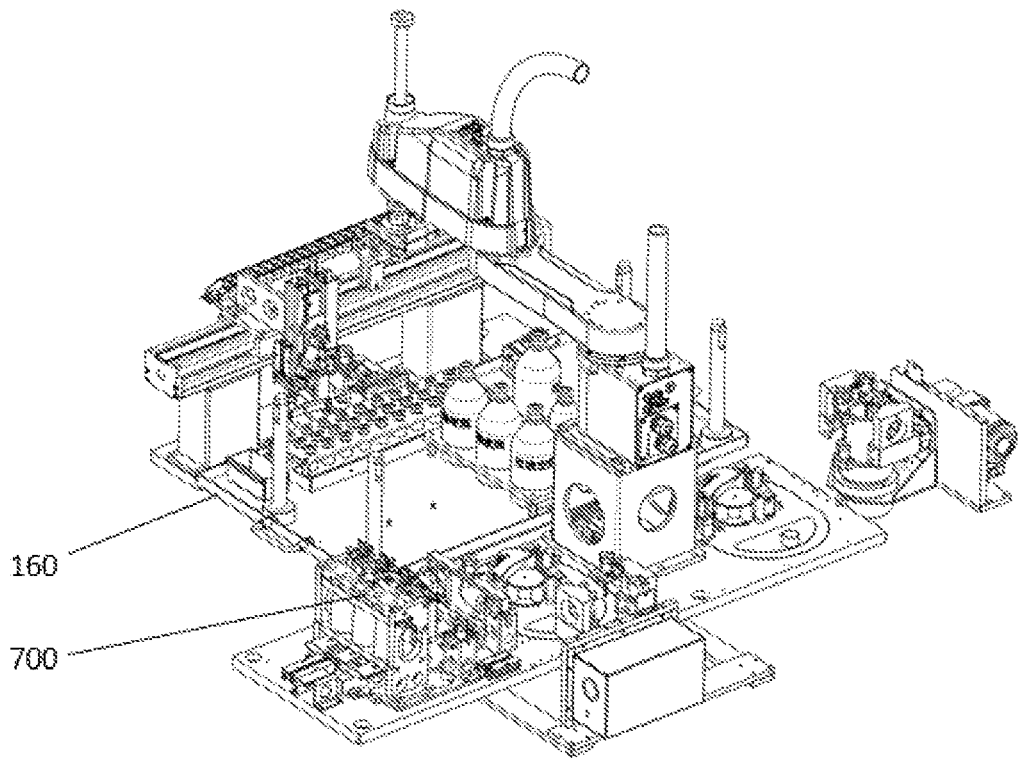
FIG. 28 is an overall structure view of the embodiment 3 during operating.

Referring to FIGS. 27 and 28, the embodiment 3 comprises a bottle opening module 300 (only the pumping function is used, and bottle opening function is not involved), a manipulator module 400, a peristaltic pump module 500, a flipping module 600, a control infusion module 700, and a third tray module 160.

The difference between the embodiment 3 and the embodiment 2 is that the test sample on the third tray module 160 is different from that of the embodiment 2, and the transition bottle 119 is filled with a dissolving liquid to dissolve powder in the vial.

Figure 29:
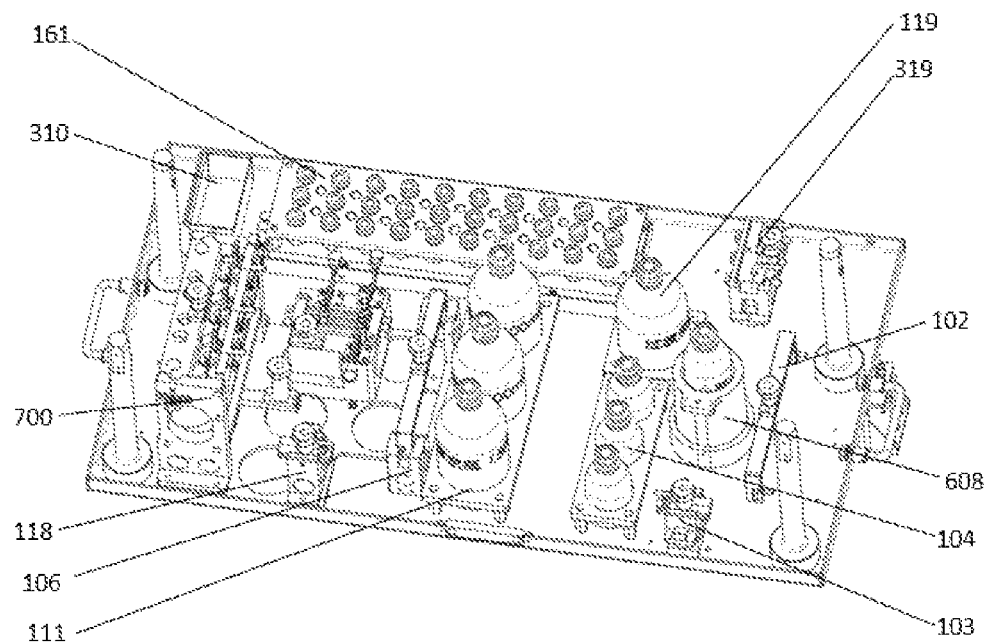
FIG. 29 is a structure view of a tray module in the embodiment 3.

Referring to FIG. 29, the third tray module 160 comprises a tray, a vial assembly (comprising a vial and a vial fixing plate), a discharging groove 310, the control infusion module 700, a moisturizing cleaning solution bottle 111, a transition bottle 119, a three-needle tooling 319, tray support rods 120, a second needle 103, a second hose mounting assembly 102, a culture medium bottle 104, and a container adaptor 608.

Operation process of the embodiment 3 is as follows:

An initial state of the control infusion module 700 is: the upper cap stopper blocks the hole on the top of the culture bottle, and the lower cap stopper 705 blocks the liquid outlet port at the bottom of the culture bottle; and the three horizontal clamps are all opened.

Step 1. Washing the culture bottle: which is the same as that of the embodiment 1.

Step 2. Dissolving the powder in the vial:

the manipulator module 400 grips and moves the transition bottle 119, which is filled with the dissolving liquid, on the tray, places it in the flipping mechanism 601, and holds it tightly; the manipulator module 400 grips and moves the second hose mounting assembly 102 and places it in the hose mounting assembly installation slot of the first peristaltic pump 501; the manipulator module 400 clamps and moves the three-needle tooling 319 in the tray to fix it with the needle mounting plate 318. The manipulator module 400 grips and moves the second needle 103 in the tray and inserts it into the transition bottle 119. The second push rod motor 314 moves the push rod downwards to insert the second needle 103 into a set of the vials containing the water-soluble solid test sample; the flipping mechanism module 600 turns the transition bottle 119 upside down, the first peristaltic pump 501 is turned on to rotate reversely, so as to transfer the dissolving liquid to the vial; then the first peristaltic pump 501 is turned off when the transferred dissolving liquid reaches the preset volume; the second push rod motor 314 moves the push rod downwards to pull the needle inserted into the vial to the mouth of the vial without complete leaving the vial; the flipping mechanism module 600 turns the transition bottle 119 upright, and the first peristaltic pump 501 is turned to rotate forward, in such a manner that the dissolving solution remaining in the hose can return to the transition bottle 119; then the first peristaltic pump 501 is turned off; the second push rod motor 314 moves the push rod downwards to completely pull out the needle inserted into the vial, and moves the needle to a next set of the vials containing the water-soluble solid test sample; all the vials can be filled with the dissolving solution by repeating the above process.

Step 3. Transferring the dissolved powder in the vial to the transition bottle 119: which is the same as that of pumping the test sample from the ampoule to the transition bottle in the embodiment 2.

Step 4. Transferring the test sample in the transition bottle 119 to the culture bottle: which is the same as that of transferring the moisturizing cleaning solution to the culture bottle, except that the moisturizing cleaning solution bottle is replaced with the transition bottle.

Step 5. Transferring a medium in the medium bottle 104 to the culture bottle: which is the same as that of the embodiment 1 or 2.

Step 6. completing the bacteria collection: which is the same as that of the embodiment 1 or 2.

What is claimed is:

1. An intelligent bacteria collection system, comprising: a guide rail, a tray module, a manipulator module, a peristaltic pump module, a flipping mechanism module, and a control infusion module; wherein the tray module is placed on the guide rail; the peristaltic pump module is provided on one side of the tray module, and a tray positioning device is provided on the other side of the tray module; the manipulator module and the peristaltic pump module are fixed on an infusion operation platform; the infusion operation platform is equipped with a liquid outlet device; the control infusion module is placed on the tray module, which is transported to and fixed on the infusion operation platform by the manipulator module;

the tray module comprises: a tray, a moisturizing cleaning solution bottle, a culture medium bottle, a test sample, a container adaptor, and the control infusion module placed on the tray; wherein the tray is used to place items, and the moisturizing cleaning solution bottle is used to clean a culture bottle in the control infusion module; the container adaptor is used to place the culture medium bottle to facilitate grasping of a flipping mechanism; the control infusion module is used for infusion and bacteria collection of the culture bottle;

the control infusion module comprises a first hose mounting assembly, a first needle, a fixed support plate, a tube fixing seat, a horizontal clamp, a culture device tooling, a tube clamp, a movable blade knife and the culture bottle; wherein the fixed support plate fixes and supports all parts; the first hose mounting assembly comprises a hose clamp and one or more infusion tubes; the infusion tubes are fixed on the hose clamp, and one end of each of the infusion tubes is connected to the first needle through a pipeline, and the other end of each of the infusion tubes is connected to a culture bottle inlet through the horizontal clamp, the tube clamp, and the movable blade knife in turn; the culture bottle is placed in the culture device tooling; a cap stopper fixing assembly, the tube clamp and the movable blade knife are provided on a top of the culture device tooling; an under-bottle pipe blocking assembly is provided on the fixed support plate at a bottom of the culture device tooling; one side of the movable blade knife is connected to a tension spring; an infusion tube installation hole and an upper cap stopper are arranged on a top of the culture bottle; an under-bottle pipe is arranged at a bottom of the culture bottle; a filter is provided inside the culture bottle; liquid in the culture bottle is discharged to a liquid outlet device through the under-bottle pipe; the cap stopper fixing assembly is arranged opposite to the upper cap stopper to drive the upper cap stopper to move vertically relative to the culture device tooling; the under-bottle pipe is arranged opposite to a lower cap stopper in the under-bottle pipe blocking assembly to drive the lower cap stopper to move vertically;

the peristaltic pump module comprises a first peristaltic pump and a second peristaltic pump; each of the peristaltic pumps has a hose mounting assembly installation slot; the flipping mechanism module comprises a first flipping mechanism and a second flipping mechanism; the first flipping mechanism is provided on one side of the first peristaltic pump, and the second flipping mechanism is provided on one side of the second peristaltic pump; the first flipping mechanism and the first peristaltic pump are provided on one side of the manipulator module, and the second flipping mechanism and the second peristaltic pump are provided on the other side of the manipulator module;

a first imitation bottle head is provided on the container adaptor, a second imitation bottle head is provided on the first hose mounting assembly, a third imitation bottle head is provided on the first needle, a fourth imitation bottle head is provided on the tube fixing seat, a fifth imitation bottle head is provided on the cap stopper fixing assembly, and a sixth imitation bottle head is provided on the under-bottle pipe blocking assembly.

2. The intelligent bacteria collection system, as recited in claim 1, further comprising: a bottle opening module opposite to the peristaltic pump module; wherein the tray module further comprises a transition bottle, a multi-needle tooling, a discharging groove, a second needle, and a second hose mounting assembly; the second hose mounting assembly comprises a hose clamp and one or more infusion tubes; the infusion tubes are fixed on the hose clamp, and one end of each of the infusion tubes is connected to the second needle through a pipeline, and the other end of each of the infusion tubes is connected to a liquid outlet of the multi-needle tooling; a quantity of the infusion tubes is equal to a quantity of the liquid outlet of multi-needle tooling; a seventh imitation bottle head is provided on the multi-needle tooling; a needle mounting plate is provided in the bottle opening module; the discharging groove is used to contain bottle head wastes generated by the bottle opening module after bottle opening.

3. The intelligent bacteria collection system, as recited in claim 2, wherein the transition bottle is filled with a dissolving liquid.

4. The intelligent bacteria collection system, as recited in claim 2, wherein the bottle opening module comprises a linear module, a bottle opening lifting cylinder, a liquid pumping lifting cylinder, a bottle head nesting plate, a breaking plate, a top cover plate, a top cover cylinder, a bottle opening breaking cylinder, the needle mounting plate, and a pin cylinder; the bottle opening lifting cylinder and the liquid pumping lifting cylinder are connected to and driven by the linear module to move horizontally; the bottle opening lifting cylinder is connected to and drives the bottle head nesting plate to move vertically; the top cover plate is arranged above the bottle head nesting plate, and is connected to and driven by the top cover cylinder to move horizontally; the top cover plate and the top cover cylinder are both set on the bottle opening lifting cylinder to move with the bottle head nesting plate; the bottle head nesting plate is connected to and driven by the bottle opening breaking cylinder through the breaking plate, so as to move horizontally; the liquid pumping lifting cylinder is connected to and drives the needle mounting plate to move vertically; the pin cylinder and a clip slot are arranged on the needle mounting plate, which are matched with mounting holes of the multi-needle tooling to fix the multi-needle tooling; a bottle head nesting hole is drilled on the bottle head nesting plate, and a rubber band is placed in the bottle head nesting hole.

5. The intelligent bacteria collection system, as recited in claim 2, wherein the bottle opening module comprises a body, a linear module, a bottle opening device, a discharging device, and a liquid pumping device; the linear module, the bottle opening device, the discharging device and the liquid pumping device are all arranged on the body; the linear module is arranged on a top of the body, and is connected to the bottle opening device, the discharging device and the liquid pumping device through a module adapter plate; the module adapter plate is connected to a connecting plate on the linear module; the bottle opening device and the discharging device are arranged on one side of the module adapter plate, and the liquid pumping device is arranged on the other side of the module adapter plate; the bottle opening device comprises a first push rod motor, an inclined breaking plate, and a spring push rod; the first push rod motor is fixed on the one side of the module adapter plate, and the inclined breaking plate is fixed on an output shaft of the first push rod motor, in such a manner that the first push rod motor drives the inclined breaking plate to move vertically; during bottle opening, a discharge side of the bottle opening device is arranged opposite to an inlet side of the discharging device; the pumping device comprises a second push rod motor, an intermediate connecting plate, a suction needle adapter, and the needle mounting plate; the second push rod motor is arranged on the other side of the module adapter plate; the intermediate connecting plate is fixed on an output shaft of the second push rod motor, and is connected to the suction needle adapter; the needle mounting plate is also connected to the suction needle adapter; the needle mounting plate is used to fix the multi-needle tooling.

6. The intelligent bacteria collection system, as recited in claim 1, wherein tray support rods are provided at four corners of the tray for stacking multiple trays.

7. The intelligent bacteria collection system, as recited in claim 2, wherein tray support rods are provided at four corners of the tray for stacking multiple trays.

8. The intelligent bacteria collection system, as recited in claim 4, wherein tray support rods are provided at four corners of the tray for stacking multiple trays.

9. The intelligent bacteria collection system, as recited in claim 5, wherein tray support rods are provided at four corners of the tray for stacking multiple trays.

10. The intelligent bacteria collection system, as recited in claim 1, wherein quantities of the horizontal clamp, the culture device tooling, the tube clamp, the movable blade knife, and the culture bottle are identical and corresponding to each other, and are equal to a quantity of the infusion tubes in the first hose mounting assembly.

11. The intelligent bacteria collection system, as recited in claim 1, wherein the culture device tooling comprises a first culture device tooling, a second culture device tooling, a third culture device tooling, and a fourth culture device tooling; the cap stopper fixing assembly, the tube clamp and the movable blade knife are provided on a top of the culture device tooling; the first culture device tooling and the second culture device tooling are fixed on the fixed support plate, which fix left and right sides of the culture bottle and limit the cap stopper fixing assembly; the third culture device tooling is mounted on middle top portions of the first culture device tooling and the second culture device tooling, which fixes the top of the culture bottle, as well as limits and fixes the clamp tube and the movable blade knife; the fourth culture device tooling is mounted on middle portions of the first culture device tooling and the culture device tooling, which fixes a middle of the culture bottle; the under-bottle pipe blocking assembly is provided on the fixed support plate at the bottom of the culture device tooling.

12. The intelligent bacteria collection system, as recited in claim 1, wherein the cap stopper fixing assembly comprises an upper cap stopper clamping plate and an upper cap stopper fixing plate; cooperating holes are arranged between the upper cap stopper clamping plate and the upper cap stopper fixing plate.

13. The intelligent bacteria collection system, as recited in claim 11, wherein the cap stopper fixing assembly comprises an upper cap stopper clamping plate and an upper cap stopper fixing plate; cooperating holes are arranged between the upper cap stopper clamping plate and the upper cap stopper fixing plate.

14. The intelligent bacteria collection system, as recited in claim 1, wherein the under-bottle pipe blocking assembly adopts a lever structure.

15. The intelligent bacteria collection system, as recited in claim 11, wherein the under-bottle pipe blocking assembly adopts a lever structure.

16. The intelligent bacteria collection system, as recited in claim 1, wherein the liquid outlet device comprises a liquid outlet diversion tank, a feeding cylinder, and a waste liquid recovery tank; a hole is drilling on a top of the liquid outlet diversion tank which has a hollow inside; a liquid outlet port is provided at a bottom of the liquid outlet diversion tank, and the waste liquid recovery tank is provided at the liquid outlet port; the feeding cylinder is connected to and drives the liquid outlet diversion tank to move forward and backward, so that the hole at the top of the liquid outlet diversion tank is connected to a liquid outlet port of the under-bottle pipe of the culture bottle.

17. The intelligent bacteria collection system, as recited in claim 1, wherein the tray positioning device comprises a cylinder and a positioning pin; the cylinder drives the positioning pin to cooperate with a side hole of the tray, thereby positioning the tray.

18. The intelligent bacteria collection system, as recited in claim 1, wherein the manipulator module comprises a mechanical arm and a mechanical gripper; the mechanical gripper comprises a bearing connector, a sliding cylinder, and a bottle head holding part; the bearing connector is connected to the mechanical arm; the sliding cylinder drives the bottle head holding part to loosen and fasten, so as to hold a bottle head or an imitation bottle head tightly.

19. The intelligent bacteria collection system, as recited in claim 1, wherein each flipping mechanism comprises a sliding table, a sliding table cylinder, and a flipping base; the sliding table is arranged on the flipping base, and is connected to the sliding table cylinder; the sliding table cylinder drives the sliding table to open and close.

* * * * *